United States Patent [19]

Bird

[11] Patent Number: 4,867,151
[45] Date of Patent: Sep. 19, 1989

[54] MOBILE SELF-CONTAINED VENTILATOR

[76] Inventor: Forrest M. Bird, P.O. Box 817, Sandpoint, Id. 83864

[21] Appl. No.: 235,704

[22] Filed: Aug. 17, 1988

Related U.S. Application Data

[63] Continuation of Ser. No. 111,138, Oct. 19, 1987, abandoned, which is a continuation of Ser. No. 901,888, Aug. 29, 1986, abandoned.

[51] Int. Cl.$^4$ .......................... A11M 16/00; A12B 7/02
[52] U.S. Cl. ........................... 128/201.17; 128/201.18; 128/205.24
[58] Field of Search ................. 128/203.12, 204.21, 128/205.18, 205.14, 205.24, 206.28, 204.18, 204.17, 203.26; 417/212; 415/125

[56] References Cited

U.S. PATENT DOCUMENTS

| | | | |
|---|---|---|---|
| 2,285,215 | 6/1942 | Lotz | 417/372 |
| 3,094,274 | 6/1963 | Thompson | 128/205.24 |
| 3,372,863 | 3/1968 | Bloom | 417/372 |
| 4,239,039 | 12/1980 | Thompson | 128/205.24 |
| 4,264,282 | 4/1981 | Crago | 417/368 |

Primary Examiner—Max Hindenburg
Assistant Examiner—K. M. Reichle
Attorney, Agent, or Firm—Flehr, Hohbach, Test, Albritton & Herbert

[57] ABSTRACT

Mobile self-contained ventilator having a framework and a compressor carried by said framework. The compressor has a motor and at least one fan driven by the motor which causes air to pass over the motor for cooling the motor and for picking up heat from the motor. The compressor also has an output through which compressed air is supplied. A respirator is carried by the framework and includes at least one oscillator cartridge having an inlet connected to the outlet for receiving compressed air from the outlet. The oscillator cartridge is disposed so that air, after it has passed over the motor, passes over the cartridge to heat the cartridge to inhibit moisture condensation within the cartridge.

6 Claims, 4 Drawing Sheets

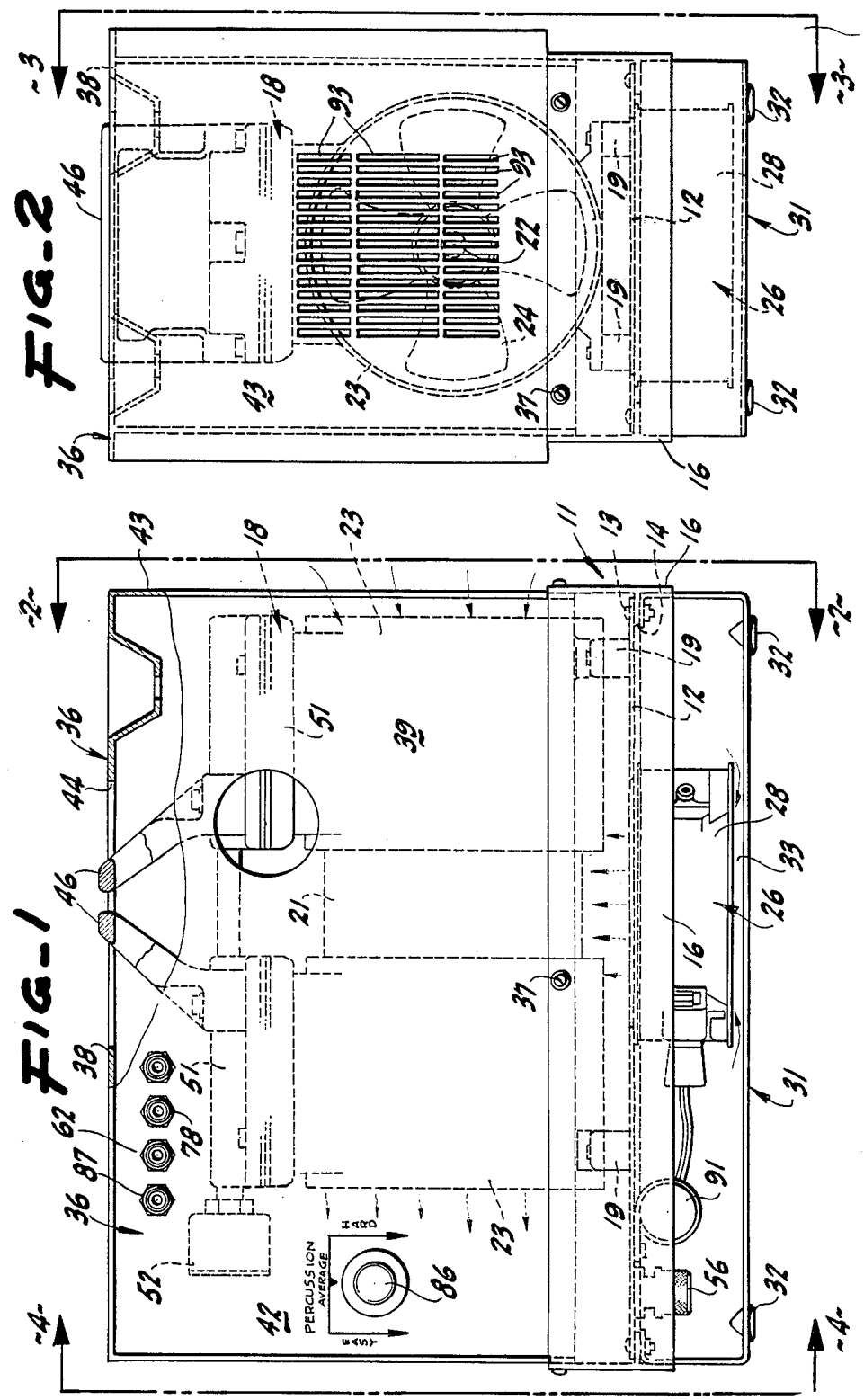

MOBILE SELF-CONTAINED VENTILATOR

This is a continuation of application Ser. No. 111,138 filed 10/19/87 which is a continuation of application Ser. No. 901,888 filed 8/29/86, both now abandoned.

This invention relates to a mobile self-contained ventilator and more particularly to a mobile self-contained intrapulmonary percussive ventilator which contains its own air compressor.

Self-contained ventilators have heretofore been provided. However, in such ventilators in the past water has condensed out from the compressed air in the components of the ventilator. This water creates numerous problems in the components such as corrosion, sticking of valves and the like which often impairs the operation of the ventilator. There is therefore a need for a new and improved self-contained ventilator which overcomes these problems.

In general, it is an object of the present invention to provide a mobile self-contained intrapulmonary percussive ventilator which utilizes a compressor driven by an electric motor which gives off heat.

Another object of the invention is to provide a ventilator of the above character in which the heat generated is utilized for heating components of the ventilator to inhibit condensation of moisture in the components of the ventilator.

Another object of the invention is to provide a ventilator of the above character in which thermal balance is provided within the housing for the components of the ventilator.

Another object of the invention is to provide a ventilator of the above character in which any condensation of moisture from the compressed air occurs in the tubing outside the housing and serves to humidify the air supplied to the patient.

Another object of the invention is to provide a ventilator of the above character in which the inspiratory-expiratory ratios may be preprogrammed.

Additional objects and features of the invention will appear from the following description in which the preferred embodiments are set forth in detail in conjunction with the accompanying drawing.

FIG. 1 is a side elevational view of a ventilator incorporating the present invention.

FIG. 2 is an elevational view taken along the line 2—2 of FIG. 1.

Figure 3:
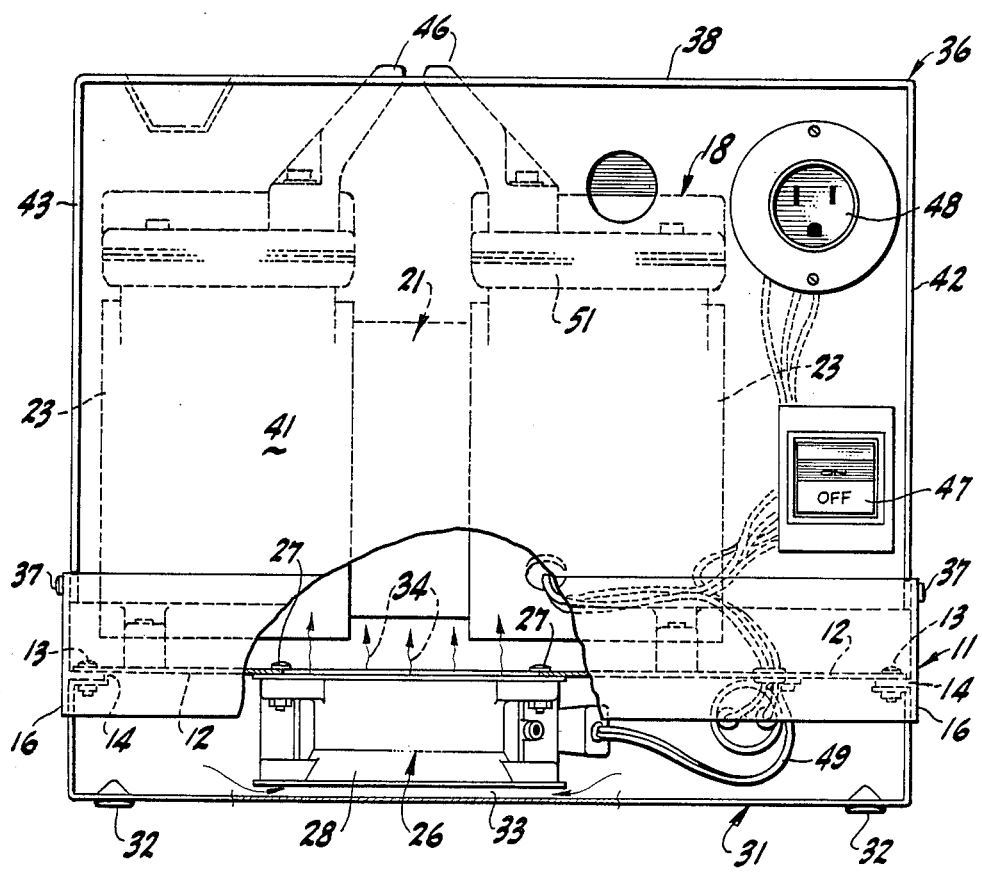
FIG. 3 is an elevational view taken along the line 3—3 of FIG. 2 with certain portions being broken away.
Figure 4:
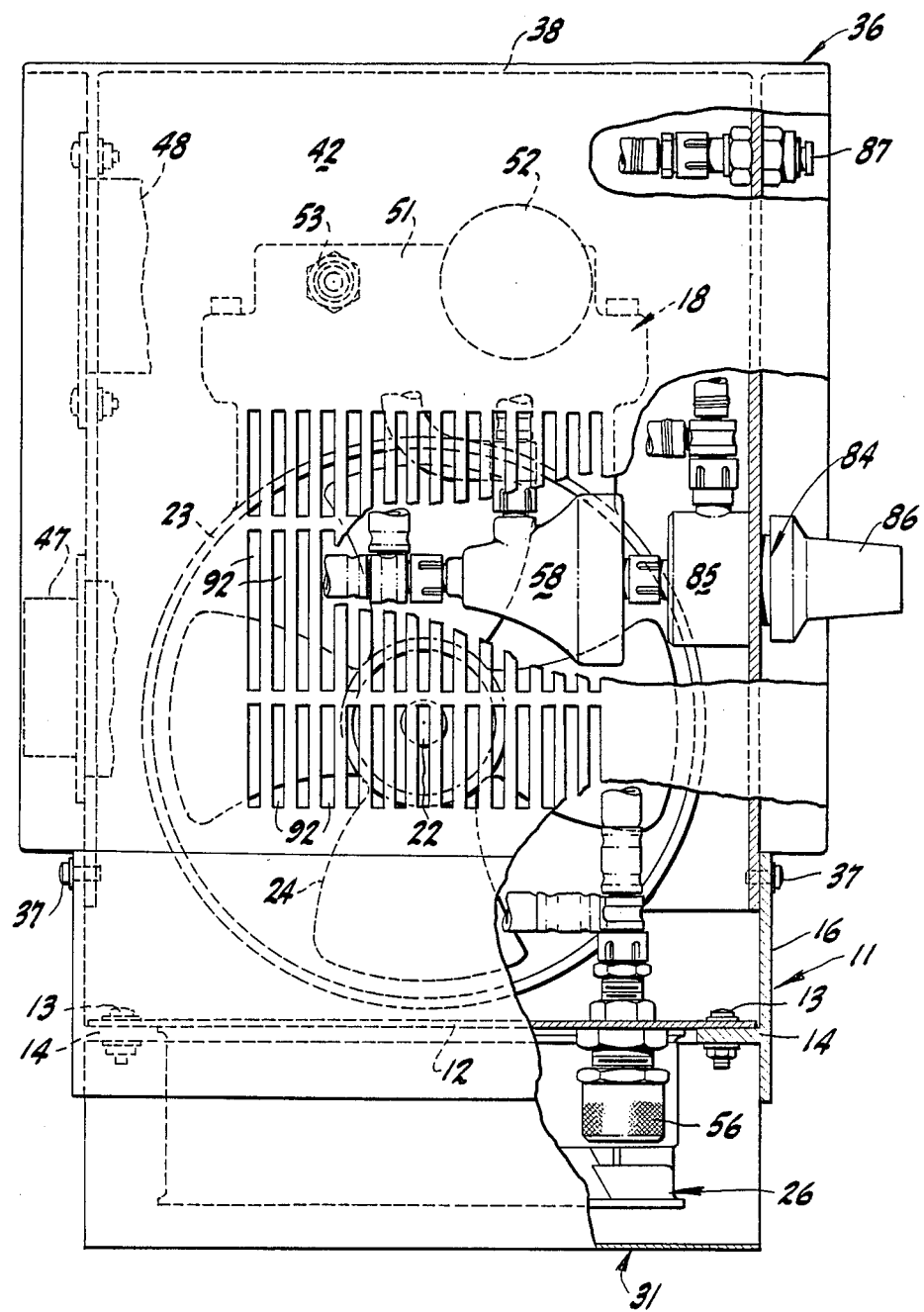
FIG. 4 is a bottom plan view taken along the line 4—4 of FIG. 3.
Figure 5:
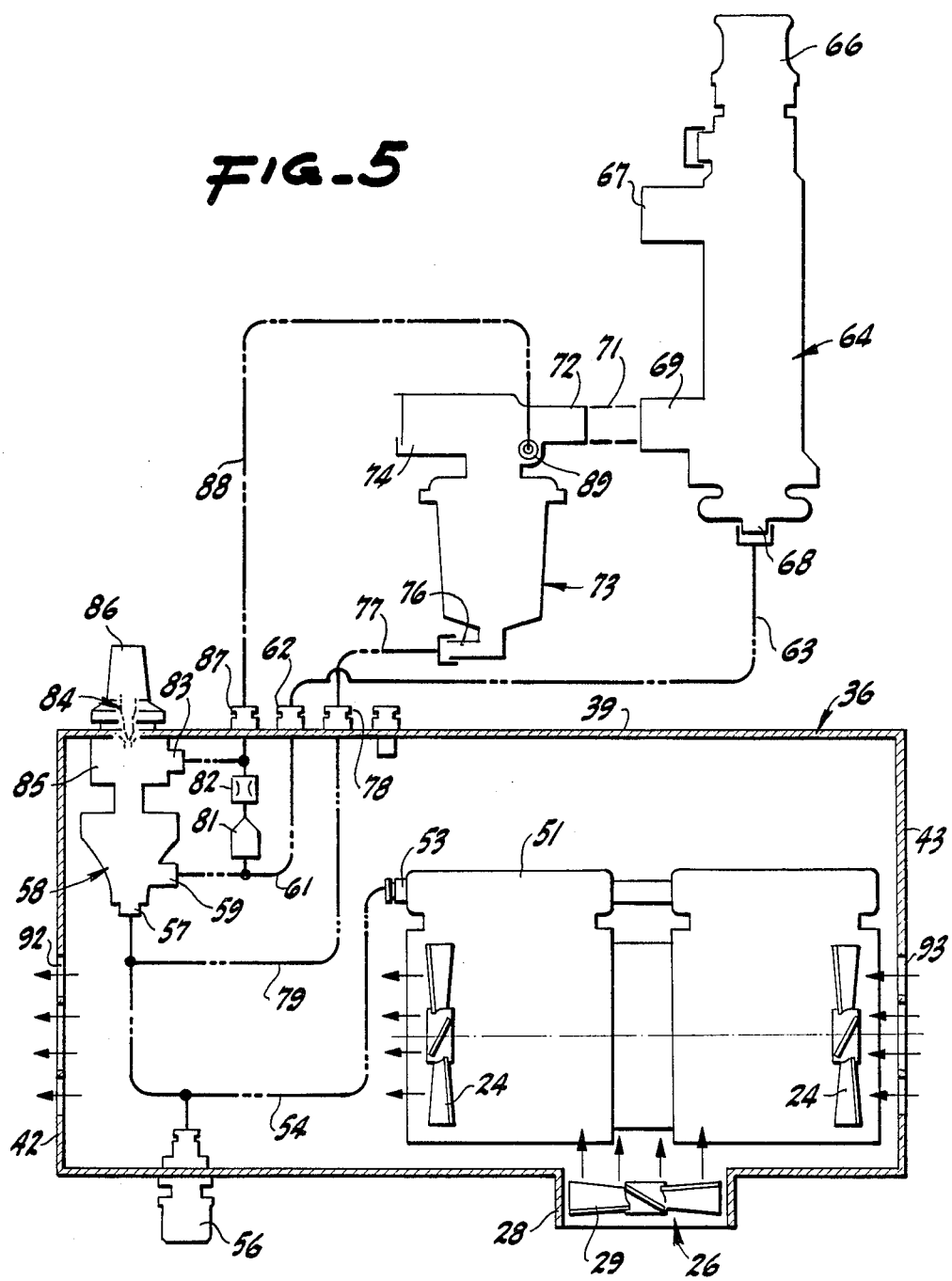
FIG. 5 is a schematic representation showing the pneumatic circuitry utilized in the ventilator shown in FIGS. 1-4.

In general, the mobile self-contained ventilator is comprised of a framework and a compressor carried by the framework. The compressor has an electric motor which gives off heat and a fan driven by the motor which causes air to be passed over the motor for cooling the motor. The compressor also has an output through which compressed air is supplied. A respirator is carried by the framework and has at least one cartridge having an inlet connected to the outlet of the compressor for receiving compressed air from the outlet of the compressor. The cartridge is disposed so that air after it has passed over the motor passes over the cartridge to heat the cartridge to inhibit water from condensation of moisture in the cartridge.

More particularly, as shown in the drawings, the mobile self-contained ventilator consists of a framework 11. The framework 11 is comprised of a rectangular metal plate 12 which is secured by suitable means such as screws 13 to two inwardly extending lips 14 formed integrally with and on opposite sides of a rectangular frame 16 formed of a suitable material such as plastic. An air compressor 18 is mounted on the metal plate 12 of the framework 11 by resilient mounting feet 19 secured to the plate 12. The air compressor 18 is of a conventional type such as the model 2618CE32-890 manufactured and sold by Thomas Industries, Inc. of Sheboygan, Wis. Such an air compressor is provided with an axially aligned electrical motor 21 which is provided with an output shaft 22. The motor 21 is mounted within a cylindrical housing 23 extending longitudinally of the framework 11. Fans 24 are mounted on opposite ends of the output shaft 22 and serve to move air from one end of the housing 23 to the other end of the housing 23 to supply cooling air to the motor 21 and to thereby remove heat generated by the motor. Additional means is provided for cooling the motor 21 and consists of a muffin-type fan 26 secured to the bottom side of the metal plate 12 of the framework 11 by suitable means such as screws 27. The fan 26 includes a generally cylindrical shroud 28 in which there is mounted a multibladed fan structure 29.

A U-shaped framework 31 is mounted within the framework 11 and is secured to the bottom side of the lips 14 by the screws 13. Four rubber grommets 32 are mounted in the lower side of the U-shaped framework 31 and serve as feet for the ventilator 11. As can be seen from FIG. 3 of the drawings, the U-shaped framework 31 is dimensioned so as to provide a space 33 between the lower extremity of the shroud 28 and the U-shaped framework 31 to permit air to pass into the fan 26 and to cause air to be directed upwardly into the compartment containing the air compressor 18 as shown by the arrows 34 in FIG. 3. This additional air provides additional cooling for the motor and this air intersects with the air passing axially over the motor 21 provided by the fans 24 so that the air from the fans 24 and the fan 26 exits from the right-hand side of the housing 23.

An enclosure 36 formed of a suitable material such as transparent plastic is mounted on the framework 11 and is secured to the upper margin of the frame 16 by suitable means such as screws 37. The enclosure is provided with a top wall 38, side walls 29 and 41 and end walls 42 and 43. The top wall 38 is provided with a rectangular opening 44 through which a pair of handles 46 extend as shown, particularly in FIG. 3. The handles 46 are secured to the air compressor 18 and form a part thereof. An on/off switch 47 as well as a female flanged electrical receptacle 48 are mounted on the side wall 41. Wiring 49 connects teh receptacle 48 to the on/off switch 47 to the air compressor 18 and to the fan 26.

The air compressor 18 includes a compressor unit 51 which is provided with an air filter 52 on its inlet. Compressed air is supplied at an outlet 53 which is connected to a pressure relief valve 56 mounted on the metal plate 12 and connected to the inlet 57 of oscillator cartridge 58. The oscillator cartridge 58 is of the type described in co-pending application Serial No. 866,791, filed May 23, 1986, and is provided with a valve member movable between open and closed positions with respect to the flow passage between the inlet 57 and the outlet 59 to control the flow through the outlet 59 from the inlet 57. The outlet 59 is connected to tubing 61 which is connected to a fitting 62 provided on the wall 39. The fitting 62 is connected by tubing 63 through a combination venturi assembly and exhalation valve 64 often called a Phasitron of the type described in U.S. Pat. No. 4,592,349. The combination venturi and exhalation valve assembly 64 is provided with a mouthpiece 66 which serves as a patient adapter to be coupled to the airway of the patient. The assembly and valve 64 is also provided with an outlet 67. The tubing 63 is connected to one inlet 68 of the assembly 64. The assembly 64 is provided with another inlet 69 which is coupled by tubing 71 to the outlet 72 of a nebulizer 73. The nebulizer 73 is provided with an entrainment inlet 74 which can entrain ambient air. It is also provided with an inlet 76 which is connected by tubing 77 to a fitting 78 provided on the wall 39. The fitting 78 is connected by tubing 79 to the tubing 54.

The tubing 61 is also connected through a one-way valve 81 through a flow restricting orifice 82 to the inlet 83 of a manifold 85 of a needle valve assembly 84. The needle valve assembly 84 is the type described in co-pending application Serial No. 671,491, filed Nov. 14, 1984 and is mounted on the oscillator cartridge 58. The oscillator cartridge 58 and the needle valve assembly 84 are mounted on the side wall 39. The needle valve assembly 84 is provided with a control knob 86 for adjusting the rate of flow through the needle valve to the diaphragm side of the oscillator cartridge 58. The orifice 82 is also connected to an adjustable bulkhead-type fitting 87 mounted on the wall 39. The fitting 87 is connected by tubing 88 to an inlet 89 of a manually controlled valve (not shown) carried by the nebulizer and of the type described in co-pending application Ser. No. 671,491, filed Nov. 14, 1984, abandoned in favor of continuation application Ser. No. 145,734 filed Jan. 14, 1988.

A starting capacitor 91 is provided for the motor 21 for the compressor and is mounted on the lower side of the plate 12. Perforations 92 and 93 are provided in the end walls 42 and 43 of the enclosure 36 to permit the air to pass therethrough from the interior of the enclosure 36.

Operation and use of the mobile self-contained ventilator 11 may now be briefly described as follows. As soon as the compressor 18 has been turned on, after it has been connected to a suitable source of power as, for example, 110 volt 60 cycle AC through the receptacle 48 and the switch 47, the compressor 18 is placed in operation and supplies compressed air on its outlet 53. This compressed air under suitable pressure, as for example, 50 psi is supplied to the oscillator cartridge 58 which is controlled by the needle valve assembly 84. A control knob 86 provides single control programming within a 340 rotational arc. Air is supplied through the outlet 59 to the combination venturi and exhalation valve assembly 64 to supply gasses through a nozzle (not shown) contained therein to the patient adapter 66 to the airway of the patient. Additional nebulized gasses are supplied through a nebulizer 73 to the inlet 69 of the combination venturi and exhalation valve assembly 64 much in the same way as described in U.S. Pat. No. 4,592,349. As described therein, inspiratory-expiratory pulsatile inspiratory flow from 0.05 to 1.5 seconds can be achieved. Inspiratory flow rates can be adjusted up to 100 liters per minute. Aerosol generation is programmed with constant delivery for therpeutic effects from the nebulizer 73. The combination venturi and exhalation valve assembly 64 makes possible patient cycling therapeutic percussive breathing. This mode of operation is of the type described in said U.S. No. 4,592,349.

The principal feature of the present invention is the provision of means for the minimization or elimination of the condensation of moisture or water within the ventilator component within the enclosure and permitting condensation of water vapor exterior of the enclosure in the tubing leading to the patient where such water condensation is desirable to provide the desired humidification for the air being supplied to the patient. This is accomplished by causing air to pass axially of the motor for the compressor as well as transversely of the motor by the use of the fans 24 and 26 and to cause the air which has picked up heat given off by the electric motor and directs the same into one end of the enclosure 36. This provides heated air passing over the cartridge 58 and the tubing leading to and from the cartridge 58 to establish a thermal equilibrium within the enclosure and to keep those components heated at a temperature above room temperature so as to prevent, or at least inhibit, the condensation of any moisture in the air being supplied from the air compressor. After the air passes through the components in the enclosure 36 and passes outside the enclosure 36 and cools down moisture condensation can occur within the tubing 63 and 88 because the tubing is at a lower temperature. This certainly is not undesirable and in fact, it is desirable to have such condensation of moisture occurs because this moisture can be entrained by the mving airstream to humidify the air being supplied to the patient.

Thus it can be seen by providing an enclosure around the compressor and mounting certain portions of the respirator within the enclosure it is possible to heat those portions of the respirator to a temperature above ambient air so that minimal, if any, condensation will occur within the parts or components of the respirator provided within the enclosure. The fans 24 and 26 provide a dual purpose. In addition to providing the necessary cooling for the electric motor, the fans cause the air heated by the motor to be directed over the component parts of the respirator to prevent condensation of moisture in the parts of the respirator.

It is apparent from the foregoing that there has been provided a new and improved mobile self-contained ventilator which makes it possible to provide intrapulmonary percussive ventilation while at the same time minimizing condensation of moisture within the percussive flow generation components. It also permits condensation to occur outside of the enclosure for the components, thereby aiding int he humidification of the air being supplied to the patient. In addition, the ventilator is constructed in such a manner so that it can be readily fabricated. Since it is provided with a transparent outer case, the operation of the compressor and its components as well as those of the respirator can be readily observed.

What is claimed is:

1. In a mobile self-contained ventilator, a framework, an air compressor mounted on said framework, said air compressor having motor means and an adjacent compressor means and at least one fan driven by the motor means axially aligned therewith which causes a unidirectional flow of air to pass over the motor means for cooling thereof by picking up heat therefrom, said compressor means having an output through which compressed air is supplied, at least one oscillator cartridge means having an inlet connected to the outlet of the compressor means and an outlet and means for connecting said outlet to a patient said one cartridge means being mounted on the framework and in general alignement with the motor means and fan downstream thereof so that the unidirectional flow of air, after it has passed over the motor means, passes over said one cartridge means to heat said one cartridge means to inhibit moisture condensation within said one cartridge means.

2. A ventilator as in claim 1 together with an enclosure mounted on said framework and enclosing said air compressor and said one cartridge means so that a thermal balance is established within the enclosure during operation of the air compressor.

3. A ventilator as in claim 1 together with an additional fan means mounted on the fraemwork for directing air over the compressor motor means in a direction transverse of the axis of alignement of the compressor motor means and said at least one fan.

4. A ventilator as in claim 3 together with an additional housing enclosing said additional fan means.

5. A ventilator as in claim 2 wherein said means for connecting to a patient includes a patient adapter and means for connecting the outlet of said one cartridge means to the patient adapter.

6. A ventilator as in claim 5 wherein said means for connecting to a patient also includes a nebulizer disposed exterior of the enclosure in said means for connecting the outlet of said one cartridge means to said